US007737103B2

(12) United States Patent
Hloucha et al.

(10) Patent No.: US 7,737,103 B2
(45) Date of Patent: Jun. 15, 2010

(54) MULTICOMPONENT THIN-TO-THICK SYSTEM

(75) Inventors: Matthias Hloucha, Köln (DE); Danuta Bedrunka, Dormagen (DE); Rainer Hofmann, Wesseling (DE); Wolfgang von Rybinski, Düsseldorf (DE); Erik Hattemer, Düsseldorf (DE); Doris Dahlmann, Düsseldorf (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 11/451,530

(22) Filed: Jun. 12, 2006

(65) Prior Publication Data

US 2007/0004609 A1   Jan. 4, 2007

Related U.S. Application Data

(63) Continuation of application No. PCT/EP2004/013316, filed on Nov. 24, 2004.

(30) Foreign Application Priority Data

Dec. 13, 2003 (DE) ............................... 103 58 536
Mar. 4, 2004 (DE) ....................... 10 2004 010 485

(51) Int. Cl.
  *C11D 3/37* (2006.01)
  *C11D 1/00* (2006.01)
  *A61K 8/72* (2006.01)

(52) U.S. Cl. ...................... 510/293; 510/130; 510/295; 510/406; 510/439; 510/475; 424/401; 424/70.11

(58) Field of Classification Search ................. 510/130, 510/293, 295, 406, 439, 475; 424/401, 70.11
See application file for complete search history.

(56) References Cited

U.S. PATENT DOCUMENTS

| 2,082,275 | A |   | 6/1937  | Daimler |         |
|-----------|---|---|---------|---------|---------|
| 2,255,082 | A |   | 9/1941  | Orthner |         |
| 2,702,279 | A |   | 2/1955  | Funderburk |      |
| 5,004,557 | A | * | 4/1991  | Nagarajan et al. | 510/337 |
| 5,362,415 | A |   | 11/1994 | Egraz   |         |
| 5,652,208 | A |   | 7/1997  | Sramek  |         |
| 6,342,472 | B1 |  | 1/2002  | Legel   |         |
| 6,399,679 | B1 |  | 6/2002  | Meffert |         |
| 6,417,152 | B1 |  | 7/2002  | Kottwitz |        |
| 6,472,360 | B1 |  | 10/2002 | Beggs   |         |
| 6,583,103 | B1 | * | 6/2003 | Klinkhammer | 510/478 |
| 6,703,357 | B1 |  | 3/2004  | Maurer  |         |

FOREIGN PATENT DOCUMENTS

| DE | 20 24 051      |   | 12/1971 |
|----|----------------|---|---------|
| DE | 197 52 163     |   | 5/1999  |
| DE | 10 2004 007 505|   | 9/2005  |
| EP | 0 522 506      |   | 1/1993  |
| EP | 0 564 476      |   | 10/1993 |
| EP | 0 595 590      |   | 5/1994  |
| EP | 0 733 097      |   | 9/1996  |
| EP | 0 875 557      |   | 11/1998 |
| EP | 0 982 021      |   | 3/2000  |
| EP | 1 130 083      |   | 9/2001  |
| FR | 2 252 840      |   | 6/1975  |
| GB | 1 333 475      |   | 10/1973 |
| GB | 1 494 915      |   | 12/1977 |
| GB | 1 494 916      |   | 12/1977 |
| WO | WO 94/18314    |   | 8/1994  |
| WO | WO 94/23005    |   | 10/1994 |
| WO | WO 95/16023    | * | 6/1995  |
| WO | WO 96/03483    |   | 2/1996  |
| WO | WO 96/04940    |   | 2/1996  |
| WO | WO 99/06515    |   | 2/1999  |
| WO | WO 99/06516    |   | 2/1999  |
| WO | WO 00/39306    |   | 7/2000  |
| WO | WO 00/42145    |   | 7/2000  |
| WO | WO 2004/014760 |   | 2/2004  |
| WO | WO 2004/018319 |   | 3/2004  |

OTHER PUBLICATIONS

Iliopoulos, I., et al., "Viscometric Evidence of Interactions between Hyrdophobically Modified Poly(sodium acrylate) and Sodium . . . ," Langmuir, 7:617-619, XP008042857, (1991).
Panmai, et al., "Rheology of hydrophobically modified polymers with spherical and rod-like surfactant micelles," Colloids and Surfaces A 147:3-15, (1999).
Todd, et al., "Volatile silicone fluids for cosmetic formulations," Cosm. Toil. 91, 29-32 (1976).
Lochhead, R., "Encyclopedia of Polymers and Thickeners for Cosmetics," Cosm. Toil., 108:95-135, (1993).
"Verordnung uber kosmetische Mittel," pp. 100-108, (1977).
"Kosmetische Farbemittel," the Farbstoffkommission der Deutschen Forschungsgemeinschaft, Verlag Chemie, Weinheim, pp. 81-106, (1984).
Van Raay, et al., "Zur Bestimmung der proteolytischen Aktivitat . . . ,"Tenside, vol. 7:125-132 (1970).
Seng, W.P., et al., "Rheological properties of model alkali-soluable associative (HASE) polymer in ionic and non-ionic surfactant . . . ," Colloids Surf., A 154:365-382, (1999).

* cited by examiner

*Primary Examiner*—Brian P Mruk
(74) *Attorney, Agent, or Firm*—David P. LeCroy

(57) ABSTRACT

The invention relates to an aqueous multicomponent system comprising a hydrophobe modified polymer which forms a high-viscosity liquid during mixing and to the use of said multicomponent system, in particular, in the form of a cosmetic component or a washing and/or rinsing and/or cleaning agent.

20 Claims, No Drawings

MULTICOMPONENT THIN-TO-THICK SYSTEM

CROSS-REFERENCE TO RELATED APPLICATIONS

This application is a continuation under 35 U.S.C. §365(c) and 35 U.S.C. §120 of International Application No. PCT/EP2004/013316, filed Nov. 24, 2004. This application also claims priority under 35 U.S.C. §119 of German Patent Application Nos. 103 58 536.2, filed Dec. 13, 2003, and 102004010485.9, filed Mar. 4, 2004. The International Application and the two German Applications are incorporated herein by reference in their entireties.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION (1) Field of the Invention

This invention relates to a multicomponent system which forms a high-viscosity liquid on mixing and to the use of this multicomponent system, more particularly as a cosmetic preparation or as a laundry detergent and/or dishwashing detergent and/or cleaner.

There is a general need in practice for cleaners with a high viscosity to achieve an extended contact time with the surface and thus to improve the cleaning effect. However, a problem with high-viscosity liquids is that they are difficult to handle in practice. For example, high-viscosity cleaners are difficult, if not impossible, to dose or to apply by spraying.

(2) Description of Related Art, Including Information Disclosed Under 37 C.F.R. §§1.97 and 1.98

One solution to this problem would be, for example, to produce the high-viscosity cleaner at the point of application itself. Low-viscosity cleaners which only assume a relatively high viscosity on dilution with water were developed to achieve this goal. For example, EP 0 595 590 describes a concentrate which contains amine oxides, an anionic alkyl detergent, a hydrophobically modified polymer and a diluent. This concentrate forms a high-viscosity liquid on addition of 96 to 98 parts water.

Accordingly, the problem addressed by the present invention was to find alternatives which would enable a high-viscosity liquid to be made available at the point of application itself. More particularly, the problem addressed by the present invention was to provide an easier-to-handle alternative to the systems described in the prior art.

Another problem addressed by the present invention was to improve the outflow behavior of the mixture in relation to the prior art and/or to provide for better thickening than achieved with conventional thickener systems.

The articles by Iliopoulos et al. (1991), Langmuir 7, 617-619 and Panmai et al. (1999), Colloids and Surfaces A 147, 3-15 describe liquids which contain hydrophobically modified polymers and which pass through a viscosity maximum on addition of surface-active substances.

It has now surprisingly been found that a highly viscous liquid, more particularly one which advantageously satisfies the requirements of a cleaner with an extended contact time, can be formed from at least two particular low-viscosity liquids, of which at least one contains a hydrophobically modified polymer and of which at least one other contains a mixture of a hydrophobically modified polymer and detergents, by mixing in a suitable ratio.

Greater product adhesion to surfaces and hence a longer contact time are achieved in this way, affording the consumer visualization in addition to the increased cleaning effect.

BRIEF SUMMARY OF THE INVENTION

Accordingly, the present invention relates to a process for the production of a high-viscosity liquid, characterized in that at least two, preferably low-viscosity, liquids are mixed with one another, the first of the at least two liquids containing at least one hydrophobically modified polymer and the second of the at least two liquids containing at least one hydrophobically modified polymer and at least one surfactant.

Accordingly, the present invention also relates to a multicomponent system, preferably a two-component system, comprising a) a first aqueous liquid containing at least one hydrophobically modified polymer and
b) a second aqueous liquid containing at least one hydrophobically modified polymer and at least one surfactant.

In addition to using a two-component system, it is also possible in accordance with the invention to use a system of more than two components. In a preferred embodiment, however, the multicomponent system is a two-component system. To use the multi-component system, the components are mixed with one another in a suitable ratio, the ratio between the first and second aqueous liquids where a two-component system is used preferably being between 1:2 and 100:1.

BRIEF DESCRIPTION OF THE SEVERAL VIEWS OF THE DRAWING(S)

Not Applicable

DETAILED DESCRIPTION OF THE INVENTION

According to the invention, the quantity of hydrophobically modified polymer in the two liquids is preferably up to 5% by weight and more preferably between 0.1 and 2% by weight.

The first aqueous liquid of the multicomponent system does not have to contain a surfactant and, in a preferred embodiment, does not contain a surfactant. In another preferred embodiment, however, the first liquid contains small quantities of surfactant, preferably between 0 and 0.4% by weight and more particularly between 0 and 0.1% by weight. Here, too, any surfactant or surfactant mixture may be used, more particularly a surfactant selected from the same group as the surfactant of the second liquid. In a preferred embodiment, the same surfactants are present in the first and second liquids.

The quantity of surfactant in the second liquid is preferably between 0.05 and 20%, more particularly between 0.1 and 12% and, above all, between 0.2 and 8% by weight.

Hydrophobically Modified Polymer

The hydrophobically modified polymer may be, for example, a hydrophobically modified polyacid, a hydrophobically modified polyamide, a hydrophobically modified polyalcohol, more particularly a hydrophobically modified polysaccharide, such as a hydrophobically modified cellulose derivative for example, or mixtures thereof. Hydrophobically modified polyacrylic acid and polymethacrylic acid amides and hydrophobically modified polyacrylates and polymethacrylates are preferred for the purposes of the invention, hydrophobically modified polyacrylates and polymethacrylates being particularly preferred.

The hydrophobically modified polymer may have any structure. For example, it may be linear, branched, have tooth-like projections like those on a comb and/or be star-shaped.

The hydrophobically modified polymer may also be a copolymer or a block copolymer. Besides units with the above-mentioned groups, i.e. acid, amide or alcohol groups, the copolymer and/or block copolymer may also comprise units that do not contain any functional units, such as for example, alkyl or polyalkylene glycol groups. The hydrophobically modified polymer may also comprise spacers which join various polymer units of the same or different length to one another, the spacer being any chemical unit, for example, an alkyl group, an alkoxy group or a polyurethane group.

According to the invention, hydrophobically modified means that hydrophobic groups are linked to the polymer, preferably to one or more functional groups of the polymer. Accordingly, the linkage is preferably in the form of an ester linkage to carboxylic acid groups or in the form of an amide linkage to carbamide groups or in the form of a urethane linkage. Alternatively, however, the hydrophobic group may also be attached to the polymer backbone by an alkylene group, more particularly a $C_{1-6}$ alkylene group, preferably a methylene group.

The degree of modification indicates the ratio between the number of monomer units of the polymer and the number of hydrophobically modifying groups or, particularly in the case of linkage to functional groups and providing all monomers comprise functional groups, the number of functional groups modified by hydrophobic groups, based on the total number of functional groups.

According to the invention, the hydrophobic group may comprise, for example, an alkyl group, an aromatic group or a polyether group and may be linear or branched. In this case, the hydrophobic group is preferably an alkyl group with a length of $C_8$ to $C_{50}$, preferably $C_8$ to $C_{26}$, more particularly $C_{12}$ to $C_{22}$, above all $C_{16}$ to $C_{20}$ and most preferably $C_{18}$ or a polyalkylene glycol, more particularly a polyethylene glycol, a polypropylene glycol or a copolymer of oxyethylene and oxypropylene units with preferably 2 to 50 and more preferably 2 to 30 recurring units, the terminal hydroxy group of the polyalkylene glycol preferably being esterified or etherified, the ester linkage preferably being formed with an acid selected from a $C_{5-50}$ carboxylic acid, more particularly a $C_{8-26}$ carboxylic acid and most preferably a $C_{16-20}$ carboxylic acid, and the ether linkage preferably being formed with a $C_{5-50}$ alcohol, more particularly a $C_{8-26}$ alcohol and most preferably a $C_{16-20}$ alcohol.

In a preferred embodiment, the hydrophobically modified polymer is a hydrophobically modified polyacrylate or a derivative thereof, the polyacrylate being hydrophobically modified by alkyl groups which are linked to carboxyl groups of the polyacrylate, more particularly by ester linkage or acid amide linkage.

In one particular embodiment, the hydrophobically modified polymer may be a polymer which comprises units of the formula —$CH_2$—$C(R^1)(W)$— and units of the formula —$CH_2$—$C(R^2)([X]_m$—$[Y]_n$—$[B]_o$—$Z$—$H)$—, where $R^1$ and $R^2$ independently of one another represent hydrogen, $C_{1-6}$ alkyl, COOH or $COOR^5$, preferably hydrogen or methyl, W stands for COOH, $COOR^3$, $CONH_2$, $CONHR^3$ or $CONR^3R^4$, preferably for COOH, $R^3$ represents $(C_{1-6})$alkyl, $(C_{1-6})$-alkyl-$SO_3H$, $(C_{1-6})$-alkyl-$PO_3H$ or $(C_{1-6})$-alkyl-$CO_2H$, the $(C_{1-6})$-alkyl group preferably being methyl, $R^4$ and $R^5$ independently of one another represent $C_{1-6}$ alkyl, X represents $C(O)O$—, $C(O)NH$— or $(C_{1-6})$alkylene, more particularly methylene, preferably $C(O)O$—, Y represents $(C_{1-4})$ oxyalkylene, more particularly oxyethylene and/or oxypropylene, in a mixed or block-like arrangement, B represents CO, Z represents $(C_{5-50})$ alkylene, preferably $(C_{5-35})$ alkylene, m is 0 or 1, preferably 1, n has a value of 0 to 50, preferably 0 to 30, o is 0 or 1.

All the above-mentioned hydrocarbon radicals and, independently thereof, the backbone of the polymer may also be substituted one or more times, more particularly by substituents selected from halogen, more particularly fluorine, chlorine or bromine, hydroxy, alkoxy, more particularly $C_{1-6}$ alkoxy, amino, alkylamino, more particularly $C_{1-6}$ alkylamino, aryl, more particularly $C_{6-10}$ aryl, aryl alkyl, more particularly $C_{6-10}$-aryl-$C_{1-6}$-alkyl, carboxy, carboxy ester, more particularly carboxy-$C_{1-6}$alkyl ester, and cycloaliphatic radicals.

The hydrophobically modified polymer or its derivative preferably has a molecular weight below 100,000 kDa, more preferably between 10 and 1,000 kDa and most preferably between 50 and 600 kDa.

The degree of modification of the hydrophobically modified polymer is preferably between 1 and 10%, more preferably between 2 and 5% and above all between 2.5 and 3.5%.

Examples of hydrophobically modified polymers suitable for use in accordance with the invention are Acusol 801 S, Acusol 820, Aculyn 22 (Acrylates/Steareth-20 Methacrylate Copolymer) and Aculyn 28 (Acrylates/Beheneth-25 Methacrylate Copolymer) from Rohm and Haas, Pemulen TR-1, Pemulen TR-2, Carbopol ETD2020 and Carbopol Ultrez 20 Polymer (all Acrylates/C10-30 Alkyl Acrylate Crosspolymer) and Carbopol Aqua SF-1 from Noveon, Structure 3001 (Acrylates/Ceteth-20 Itaconate Copolymer) and Structure 2001 (Acrylates/Palmeth-25 Itaconate Copolymer) from National Starch, Synthalen W2000 (Acrylates/Palmeth-25 Acrylate Copolymer) from 3V Sigma and Aristoflex HMB from Clariant.

In a particularly preferred embodiment, the hydrophobically modified polymer is a hydrophobically modified polyacrylate, the polyacrylate being hydrophobically modified by alkyl groups linked to carboxyl groups of the polyacrylate, more particularly by ester linkage or by acid amide linkage, and the alkyl groups being those with a length of $C_8$ to $C_{26}$, preferably between $C_{12}$ and $C_{22}$, more particularly, between $C_{16}$ and $C_{20}$ and most preferably with a length of $C_{18}$.

In another particularly preferred embodiment, the hydrophobically modified polyacrylate is the polymer commercially available under the name of Acusol 801 S or Acusol 820 (Rohm and Haas).

Surfactants

The surfactant suitable for use in accordance with the invention is preferably a surfactant selected from the group consisting of anionic surfactants, amphoteric surfactants and nonionic surfactants or mixtures thereof. Cationic surfactants may be present in small quantities as addition components.

Suitable anionic surfactants are, for example, those of the sulfonate and sulfate type. Suitable surfactants of the sulfonate type are preferably $C_{9-13}$ alkyl benzenesulfonates, olefin sulfonates, i.e. mixtures of alkene and hydroxyalkane sulfonates, and the disulfonates obtained, for example, from $C_{12-18}$ monoolefins with an internal or terminal double bond by sulfonation with gaseous sulfur trioxide and subsequent alkaline or acidic hydrolysis of the sulfonation products. Other suitable surfactants of the sulfonate type are the alkane sulfonates obtained from $C_{12-18}$ alkanes, for example, by sulfochlorination or sulfoxidation and subsequent hydrolysis or neutralization. The esters of α-sulfofatty acids (ester sulfonates), for example, the α-sulfonated methyl esters of hydrogenated coconut oil, palm kernel oil or tallow fatty acids, are also suitable.

Other suitable anionic surfactants are sulfonated fatty acid glycerol esters. Fatty acid glycerol esters in the context of the present invention are the monoesters, diesters and triesters and mixtures thereof which are obtained where production is carried out by esterification of a monoglycerol with 1 to 3 mol fatty acid or in the transesterification of triglycerides with 0.3 to 2 mol glycerol. Preferred sulfonated fatty acid glycerol esters are the sulfonation products of saturated fatty acids containing 6 to 22 carbon atoms, for example, caproic acid, caprylic acid, capric acid, myristic acid, lauric acid, palmitic acid, stearic acid or behenic acid.

Preferred alk(en)yl sulfates are the alkali metal salts and, in particular, the sodium salts of the sulfuric acid semiesters of $C_{12-18}$ fatty alcohols, for example, cocofatty alcohol, tallow fatty alcohol, lauryl, myristyl, cetyl or stearyl alcohol, or $C_{10-20}$ oxoalcohols and the corresponding semiesters of secondary alcohols with the same chain length. Other preferred alk(en)yl sulfates are those with the chain length mentioned which contain a synthetic, linear alkyl chain based on a petrochemical and which are similar in their degradation behavior to the corresponding compounds based on oleochemical raw materials. $C_{12-16}$ alkyl sulfates, $C_{12-15}$ alkyl sulfates and $C_{14-15}$ alkyl sulfates are preferred for laundry detergents. Other suitable anionic surfactants are 2,3-alkyl sulfates which are commercially obtainable as products of the Shell Oil Company under the name of DAN®.

The sulfuric acid monoesters of linear or branched $C_{7-21}$ alcohols ethoxylated with 1 to 6 mol ethylene oxide, such as 2-methyl-branched $C_{9-11}$ alcohols containing on average 3.5 mol ethylene oxide (EO) or $C_{12-18}$ fatty alcohols containing 1 to 4 EO, are also suitable. In view of their high foaming capacity, they are only used in relatively small quantities, for example, in quantities of 1 to 5% by weight, in cleaning compositions.

Other suitable anionic surfactants are the salts of alkyl sulfosuccinic acid which are also known as sulfosuccinates or as sulfosuccinic acid esters and which represent monoesters and/or diesters of sulfosuccinic acid with alcohols, preferably fatty alcohols and, more particularly, ethoxylated fatty alcohols. Preferred sulfosuccinates contain $C_{8-18}$ fatty alcohol residues or mixtures thereof. Particularly preferred sulfosuccinates contain a fatty alcohol residue derived from ethoxylated fatty alcohols which, considered in isolation, represent nonionic surfactants (for a description, see below). Of these sulfosuccinates, those of which the fatty alcohol residues are derived from narrow-range ethoxylated fatty alcohols are particularly preferred. Alk(en)yl succinic acid preferably containing 8 to 18 carbon atoms in the alk(en)yl chain or salts thereof may also be used.

The anionic surfactants may be present in the form of their sodium, potassium or ammonium salts and as soluble salts of organic bases, such as mono-, di- or triethanolamine. The anionic surfactants are preferably present in the form of their sodium or potassium salts and, more preferably, in the form of their sodium salts.

Preferred nonionic surfactants are alkoxylated, advantageously ethoxylated, more especially primary alcohols preferably containing 8 to 18 carbon atoms and, on average, 1 to 20 and more particularly 1 to 12 mol ethylene oxide (EO) per mol alcohol, in which the alcohol component may be linear or, preferably, methyl-branched in the 2-position or may contain linear and methyl-branched residues in the form of the mixtures typically present in oxoalcohol residues. However, alcohol ethoxylates containing linear residues of alcohols of native origin with 12 to 18 carbon atoms, for example, coconut oil, palm oil, tallow or oleyl alcohol, and on average 2 to 8 EO per mol alcohol are particularly preferred. Preferred ethoxylated alcohols include, for example, $C_{12-14}$ alcohols containing 3 EO or 4 EO, $C_{9-11}$ alcohol containing 7 EO, $C_{13-15}$ alcohols containing 3 EO, 5 EO, 7 EO or 8 EO, $C_{12-18}$ alcohols containing 3 EO, EO 5 or 7 EO and mixtures thereof, such as mixtures of $C_{12-14}$ alcohol containing 3 EO and $C_{12-18}$ alcohol containing 5 EO. The degrees of ethoxylation mentioned represent statistical mean values which, for a special product, can be a whole number or a broken number. Preferred alcohol ethoxylates have a narrow homolog distribution (narrow range ethoxylates, NRE). In addition to these nonionic surfactants, fatty alcohols containing more than 12 EO may also be used, examples including tallow fatty alcohol containing 14 EO, 25 EO, 30 EO or 40 EO.

Low-foaming nonionic surfactants which contain alternating ethylene oxide and alkylene oxide units may also be used. Preferred representatives of these surfactants are those which contain EO-AO-EO-AO blocks where one to ten EO or AO groups are attached to one another before a block of the other groups follows. Examples of such surfactants are those which correspond to the following general formula:

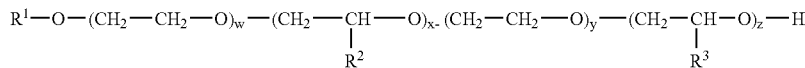

in which $R^1$ is a linear or branched, saturated or mono- or polyunsaturated $C_{6-24}$ alkyl or alkenyl group; the groups $R^2$ and $R^3$ independently of one another are each selected from —$CH_3$; —$CH_2CH_3$, —$CH_2CH_2$—$CH_3$, —$CH(CH_3)_2$ and the indices w, x, y and z independently of one another stand for integers of 1 to 6. These nonionic surfactants may be obtained by known methods from the corresponding alcohols $R^1$—OH and ethylene or alkylene oxide. The substituent $R^1$ in the above formula may vary according to the origin of the alcohol. If native sources are used, the substituent $R^1$ has an even number of carbon atoms and is generally unbranched, the linear chains of alcohols of native origin containing 12 to 18 carbon atoms, for example, of coconut oil, palm oil, tallow fatty alcohol or oleyl alcohol being preferred. Alcohols obtainable from synthetic sources are, for example, the Guerbet alcohols or 2-methyl-branched or linear or methyl-branched alcohols as normally present in oxoalcohols. Irrespective of the nature of the alcohol used to produce the nonionic surfactants present in accordance with the invention in the detergents, preferred detergents according to the invention are those where $R^1$ in the above formula is a $C_{6-24}$, preferably $C_{8-20}$, more preferably $C_{9-15}$ and most preferably $C_{9-11}$ alkyl group. Besides propylene oxide, butylene oxide in particular, may be the alkylene oxide unit which may be present in alternation with the ethylene oxide unit in the nonionic surfactants. However, other alkylene oxides where $R^2$ and $R^3$ independently of one another are selected from —$CH_2CH_2$—$CH_3$ or —$CH(CH_3)_2$ are also suitable.

Another class of suitable nonionic surfactants, which may be used either as sole nonionic surfactant or in combination with other nonionic surfactants, are alkoxylated, preferably ethoxylated or ethoxylated and propoxylated, fatty acid alkyl esters preferably containing 1 to 4 carbon atoms in the alkyl chain, more especially fatty acid methyl esters.

Another class of nonionic surfactants which may be used in accordance with the invention are the alkyl polyglycosides (APGs). Suitable alkyl polyglycosides correspond to the general formula R—O-(-G)$_z$ where R is a linear or branched, more particularly 2-methyl-branched, saturated or unsaturated aliphatic radical containing 8 to 22 and preferably 8 to 18 carbon atoms, G stands for a glycosidically linked residue of a monosaccharide and z has a value of 1 to 10.

An industrially significant synthesis for the production of APGs consists essentially in the acid-catalyzed condensation of monosaccharides of the aldose type (HO-G) with long-chain alcohols (R—OH) containing 8 to 22 and preferably 8 to 18 carbon atoms. Alkyl glycosides corresponding to formula (I):

R—O(-G)$_z$ (I)

where the value of z can be varied within wide limits through the choice of the reaction conditions, are formed in the condensation reaction which is accompanied by the elimination of water. Alkyl glycosides of formula (I) with n=1 to 10 are suitable for use in accordance with the invention. Compounds where n has a value of 1 to 6, more particularly 1 to 2, are preferred. In products where n>1, n is of course a statistical mean value.

The alkyl glycosides may also be produced from oligo- or polysaccharides which, in the acid-catalyzed reaction, are first depolymerized to lower fragments by hydrolysis and/or alcoholysis before forming the alkyl glycosides of formula I. Mixtures of various reducing monosaccharides or polysaccharides containing various monosaccharide units may be used as starting materials. If n>1, alkyl glycoside molecules of correspondingly mixed composition can be formed.

Preferred starting materials are the following monosaccharides: glucose, mannose, galactose, arabinose, apiose, lyxose, gallose, altrose, idose, ribose, xylose and talose and the oligo- and polysaccharides composed of these monosaccharides, for example, maltose, lactose, maltotriose, hemicellulose, starch, partial hydrolyzates of starch and sugar syrup. However, alkyl glycosides produced from the same monosaccharide units are preferred for the purposes of the invention. Alkyl glycosides where the residue (-G) is derived from glucose are particularly preferred. Glucose, maltose, starch and other oligomers of glucose are correspondingly used as starting materials for these compounds which are also known as alkyl glucosides.

In the above described production process, the alkyl moiety R is derived from long-chain, optionally unsaturated, preferably primary alcohols which may also be branched. Examples are the synthetic oxoalcohols containing 9 to 15 carbon atoms and the fatty alcohols containing 8 to 22 carbon atoms obtained from natural fatty acids. The $C_{8-18}$ fatty alcohols and the $C_{11-15}$ oxoalcohols are preferred, the $C_{8-10}$ or $C_{12-14}$ fatty alcohols being particularly preferred.

Another class of suitable nonionic surfactants which may be used either as sole nonionic surfactant or in combination with other nonionic surfactants are alkoxylated, preferably ethoxylated or ethoxylated and propoxylated, fatty acid alkyl esters preferably containing 1 to 4 carbon atoms in the alkyl chain.

Nonionic surfactants of the amine oxide type, for example, N-cocoalkyl-N,N-dimethylamine oxide and N-tallowalkyl-N,N-dihydroxyethylamine oxide, and the fatty acid alkanolamide type are also suitable. The quantity in which these nonionic surfactants are used is preferably no more than the quantity in which the ethoxylated fatty alcohols are used and, more preferably, no more than half that quantity.

Other suitable nonionic surfactants are polyhydroxyfatty acid amides corresponding to formula (II):

(II)

in which RCO is an aliphatic acyl group containing 6 to 22 carbon atoms, $R^1$ is hydrogen, an alkyl or hydroxyalkyl group containing 1 to 4 carbon atoms and [Z] is a linear or branched polyhydroxyalkyl group containing 3 to 10 carbon atoms and 3 to 10 hydroxyl groups. The polyhydroxyfatty acid amides are known substances which may normally be obtained by reductive amination of a reducing sugar with ammonia, an alkylamine or an alkanolamine and subsequent acylation with a fatty acid, a fatty acid alkyl ester or a fatty acid chloride.

The group of polyhydroxyfatty acid amides also includes compounds corresponding to formula (III):

(III)

in which R is a linear or branched alkyl or alkenyl group containing 7 to 12 carbon atoms, $R^1$ is a linear, branched or cyclic alkyl group or an aryl group containing 2 to 8 carbon atoms and $R^2$ is a linear, branched or cyclic alkyl group or an aryl group or an oxyalkyl group containing 1 to 8 carbon atoms, $C_{1-4}$ alkyl or phenyl groups being preferred, and [Z] is a linear polyhydroxyalkyl group, of which the alkyl chain is substituted by at least two hydroxyl groups, or alkoxylated, preferably ethoxylated or propoxylated, derivatives of that group.

[Z] is preferably obtained by reductive amination of a reduced sugar, for example, glucose, fructose, maltose, lactose, galactose, mannose or xylose. The N-alkoxy- or N-aryloxy-substituted compounds may then be converted into the required polyhydroxyfatty acid amides by reaction with fatty acid methyl esters in the presence of an alkoxide as catalyst.

Other suitable nonionic surfactants are the end-capped poly(oxyalkylated) nonionic surfactants corresponding to the following formula:

$R^1O[CH_2CH(R^3)O]_x[CH_2]_kCH(OH)[CH_2]_jOR^2$ in which $R^1$ and $R^2$ are linear or branched, saturated or unsaturated, aliphatic or aromatic hydrocarbon radicals containing 1 to 30 carbon atoms, $R^3$ stands for H or for a methyl, ethyl, n-propyl, isopropyl, n-butyl, 2-butyl or 2-methyl-2-butyl radical, x has a value of 1 to 30, k and j have values of 1 to 12 and preferably 1 to 5. Where x has a value of $\geq 2$, each substituent $R^3$ in the above formula may be different. $R^1$ and $R^2$ are preferably linear or branched, saturated or unsaturated, aliphatic or aromatic hydrocarbon radicals containing 6 to 22 carbon atoms, radicals containing 8 to 18 carbon atoms being particularly preferred. For the substituent $R^3$, H, —CH$_3$ or —CH$_2$CH$_3$ are particularly preferred. Particularly preferred values for x are in the range from 1 to 20 and more particularly in the range from 6 to 15.

Suitable amphoteric or zwitterionic surfactants which maybe used in accordance with the invention contain a basic group and an acidic group which form an inner salt. The cationic group is, in particular, a quaternary ammonium group although it may also be a phosphonium, imidazolium or sulfonium group for example. The anionic group is, in particular, a carboxylate or sulfonate group although it may also be a phosphonate or sulfate group for example.

Amphoteric surfactants preferably used in accordance with the invention are compounds corresponding to general formula (IV):

(IV)

where $R^2$ is preferably an aliphatic or aromatic hydrophobic, optionally substituted group, $R^3$ and $R^4$ independently of one another preferably represent hydrogen or a short, optionally substituted alkyl group and may even be linked to one another, $R^5$ is preferably an optionally substituted alkylene or polyalkoxy group and $X^-$ is preferably a carboxylate or sulfonate group.

Typical examples of amphoteric or zwitterionic surfactants are alkyl betaines, alkyl amidobetaines, aminopropionates, aminoglycinates, imidazolinium betaines and sulfobetaines.

A preferred embodiment is characterized by the use of betaine compounds corresponding to formula (V):

(V)

where $R^2$ is $C_{8-25}$ and preferably $C_{10-21}$ alkyl group optionally interrupted by hetero atoms or hetero atom groups and $R^3$ and $R^4$ represent like or different alkyl groups containing 1 to 3 carbon atoms. $C_{10-18}$ alkyl dimethyl carboxymethyl betaine and $C_{11-17}$ alkyl amidopropyl dimethyl carboxymethyl betaine are preferred.

Sulfobetaines are also preferred. In this case, the anionic group is a sulfonate group instead of the carboxy group. Bis(hydroxyethyl)sulfobetaine and cocoamidopropylsulfobetaine are particularly suitable. However, betaines and/or sulfobetaines as described, for example, in U.S. Pat. Nos. 2,082,275, 2,702,279 or 2,255,082 may generally be used.

In a particularly preferred embodiment, the surfactants used comprise at least one surfactant selected from the group consisting of alkyl sulfates, alkyl ether sulfates, alkyl sulfonates, alkyl aryl sulfonates, alkyl benzene sulfonates, alkyl aryl ether sulfonates, alkyl ether hydroxylates, fatty alcohol ether sulfates, LAS, APG, betaines and fatty alcohol ethoxylates, particularly from the group consisting of dodecyl sulfate, dodecyl ether sulfate and fatty alcohol ethoxylates comprising a $C_{12-18}$ fatty alcohol and, on average, less than 20 ethoxylate units, preferably 6 to 7 ethoxylate units.

The multicomponent system and particularly the two-component system may be used in different ways. Thus, the at least two components may be accommodated in at least two separate containers, for example, bottles. To prepare the highly viscous liquid, the at least two liquids may then be manually poured in measured quantities into a third container, for example, into a bucket, and then mixed together.

Alternatively, however, a multicompartment system, more particularly a two-compartment system, for example, a two-compartment spray or two-compartment bottle, may also be used. However, the liquids do not have to be manually mixed. Instead, the liquids are mixed automatically in use by the advantageous device.

The cleaning composition may also be applied from the container, more particularly from the multicompartment system, to the point of application using a spray dispenser.

The spray dispenser is preferably a manually activated spray dispenser selected in particular, from the group consisting of aerosol spray dispensers (pressurized gas containers, also known as spray cans), self-pressurizing spray dispensers, pump spray dispensers and trigger spray dispensers, more particularly pump spray dispensers and trigger spray dispensers with a container of transparent polyethylene or polyethylene terephthalate. Spray dispensers are described in more detail in WO 94/04940 (Procter & Gamble) and the US patents cited therein, to all of which reference is made in this regard and of which the disclosures are hereby included in the present application. Trigger spray dispensers and pump spray dispensers have the advantage over pressurized gas containers that no propellant has to be used.

Examples of a multicompartment container can be found in WO 04/018319 and DE 102004007505.0 and the prior art literature cited therein, of which the disclosures in relation to multicompartment containers are hereby included in the present application.

To prepare the highly viscous solution, the two components of a two-component system are preferably mixed with one another in a ratio of 1:2 to 100:1 and more preferably in a ratio of 1:1 to 50:1. The preferred mixing ratio is of course dependent on the composition of the two components.

In a preferred embodiment, the compositions of the two components of the two-component system and their mixing ratio are selected so that the viscosity of the mixture at a shear rate of $0.1~s^{-1}$ is about twice as high, three times as high, five times as high or ten times as high as the viscosity of at least one, preferably both, of the two components.

In another preferred embodiment of the multicomponent system, particularly the two-component system, according to the invention, the compositions and the mixing ratio of the components are selected so that the viscosity of the mixture at a shear rate of $0.1~s^{-1}$ is more than 10 times, more particularly more than 50 times and, above all, more than 100 times higher than the viscosity of at least one, preferably both or all, of the components used.

In preferred embodiments, the components of the multicomponent system independently of one another have viscosities at a shear rate of $0.1~s^{-1}$ of less than 100 and/or less than 200 Pas.

The viscosities were measured with a shear-stress-controlled rotational rheometer AR 1000-N (TA Instruments) comprising a plate-cone measuring system 4 cm in diameter with a cone angle of 1° in flow tests in the shear rate range of 0 to $1,000~s^{-1}$ at 20° C.

The pH value of the components of the multicomponent system and of the resulting mixture is preferably in the range from 5 to 14. The individual components of the multicomponent system and/or the resulting mixture can have different pH values.

In a preferred embodiment, at least one of the components additionally contains at least one other constituent, the choice of this other constituent being determined by the intended application.

Intended applications of the multicomponent system according to the invention include, for example, its use as a cosmetic preparation and/or as a detergent and/or cleaning composition.

The cosmetic preparation may be, in particular, a hair treatment and/or hair care preparation, for example, a hair shampoo, a hair lotion, a hair conditioner or a hair colorant, or a body care preparation, more particularly a skin treatment preparation, such as a deodorant, a sun oil or a liquid soap for example.

The detergent and/or cleaning composition may be, in particular, a fabric treatment preparation, including above all a fabric pretreatment preparation, a manual detergent, a manual dishwashing detergent, above all a pretreatment preparation for dishes, a sanitary preparation, a sterilizing preparation and/or a disinfectant.

Ingredients which are known to the expert and/or which are mentioned by way of example in the following for the hard surface cleaner, hair-care preparation and laundry pretreatment preparation embodiments may be present for the intended applications mentioned above.

Hard Surface Cleaners

Hard surfaces in the context of the present invention include, in particular, any plastic, glass, ceramic or metal surfaces typically encountered in the home, for example, kitchen surfaces, cookers, bathroom surfaces, floor tiles, laminate floors and tableware.

Where the multicomponent system is used as a hard surface cleaner, the liquids of the multicomponent system may also contain other constituents which are known to the expert for a hard surface cleaner. Besides the hydrophobically modified polymer and the surfactants mentioned above, these constituents may be, in particular, builders, acids, alkalis, hydrotropes, solvents, thickeners, abrasives, enzymes and other auxiliaries and additives, such as preservatives, dyes, fragrances (perfume), corrosion inhibitors or skin care preparations. If the cleaner is to be applied by spraying, a propellant may also be present. The various liquids of the multicomponent cleaner independently of one another may contain one or more of the above-mentioned components listed below in any combination and concentration.

Suitable builders are, for example, alkali metal gluconates, citrates, nitrilotriacetates, carbonates and bicarbonates, more particularly sodium gluconate, citrate and nitrilotriacetate and sodium and potassium carbonate and bicarbonate, and alkali metal and alkaline earth metal hydroxides, more particularly sodium and potassium hydroxide, ammonia and amines, more particularly mono- and triethanolamine, and mixtures thereof. Other suitable builders are the salts of glutaric acid, succinic acid, adipic acid, tartaric acid and benzene-hexacarboxylic acid and phosphonates and phosphates. The cleaners may contain builders in quantities, based on the composition, of 0.1 to 5% by weight.

Acids and/or alkalis on the one hand act as pH adjusters, on the other hand the acids can also contribute to the removal of lime stains from the surfaces to be cleaned. The acids suitable for use in accordance with the invention may be inorganic mineral acids, for example, hydrochloric acid, and/or $C_{1-6}$ mono-, di- or polycarboxylic acids or hydrocarboxylic acids, such as for example, formic acid, acetic acid, lactic acid, citric acid, gluconic acid, glutaric acid, succinic acid, adipic acid, tartaric acid or even malic acid, and other organic acids, such as salicylic acid or amidosulfonic acid for example. However, citric acid is particularly preferred. Mixtures of several acids may also be used. Acids may be present in the cleaner according to the invention in quantities of up to 6% by weight, based on the composition as a whole.

The bases optionally used include alkanolamines, for example, mono- or diethanolamine, and ammonium or alkali metal hydroxides, above all sodium hydroxide. The cleaner according to the invention may contain bases in quantities of up to 2.5% by weight, based on the composition as a whole.

The components of the cleaner according to the invention may additionally contain one or more thickeners for viscosity adjustment. Suitable thickeners are natural and synthetic polymers and inorganic thickeners. Suitable polymers include polysaccharides and heteropolysaccharides and other organic natural thickeners, including the polysaccharide gums, such as gum arabic, agar, alginates, carrageens and salts thereof, guar, guarane, tragacanth, gellan, ramsan, dextran orxanthan and derivatives thereof, for example, propoxylated guar, and mixtures thereof, also pectins, polyoses, locust bean gum, starch, dextrins, gelatin, casein. In addition, organic modified natural materials, such as carboxymethyl cellulose and cellulose ethers, hydroxyethyl and hydroxypropyl cellulose and the like or cellulose acetate and gum ethers, may be used. Suitable organic fully synthetic thickeners are homo- and copolymeric polycarboxylates, above all polyacrylic and polymethacrylic compounds, and vinyl polymers, polycarboxylic acids, polyethers, polyimines or even polyamides. Suitable inorganic thickeners include polysilicic acids, clay minerals, such as montmorillonites, zeolites, silica and various nanoparticulate inorganic compounds, such as nanoparticulate metal oxides, oxide hydrates, hydroxides, carbonates and phosphates and silicates with a mean particle size of 1 to 200 nm, based on the particle diameter in the longitudinal direction, i.e. in the direction of the greatest extent of the particles. In another embodiment of the invention, the nanoparticulate materials may optionally be treated with one or more surface modifiers. The surface modification is carried out in known manner with mono- or polybasic $C_{2-8}$ carboxylic acids or hydroxycarboxylic acids, functional silanes with the formula $(OR)_{4-n}SiR_n$ (R=organic residues with functional groups, such as hydroxy, carboxy, ester, amine, epoxy, etc.), quaternary ammonium compounds or amino acids and other substances known for this purpose.

Besides the thickeners mentioned thus far, the cleaner according to the invention may contain electrolyte salts. The electrolyte salts may also contribute to an increase in viscosity. Electrolyte salts in the context of the present invention are salts which decompose into their ionic constituents in the water-based cleaner according to the invention. Preferred electrolyte salts are the salts, more particularly alkali metal and/or alkaline earth metal salts, of an inorganic acid, preferably an inorganic acid from the group consisting of the hydrohalic acids, nitric acid and sulfuric acid, more particularly the chlorides and sulfates. According to the invention, an electrolyte salt may also be used in the form of its corresponding acid/base pair, for example, hydrochloric acid and sodium hydroxide instead of sodium chloride.

The above-mentioned or other organic and/or inorganic thickeners are preferably present in only small quantities in the components of the cleaner according to the invention. In a preferred embodiment, no thickeners at all are added.

In one advantageous embodiment, the components of the cleaner according to the invention may additionally contain one or more water-soluble organic solvents, typically in a quantity of up to 6% by weight, based on the composition as a whole. According to the invention, the solvent may be used as required as a hydrotrope, viscosity adjuster and/or low-temperature stabilizer. It has a solubilizing effect in particular, for surfactants and electrolyte and also for perfume and dye and thus contributes to their incorporation, prevents the formation of liquid crystalline phases and shares in the formation of clear products. The viscosity of the cleaner according to the invention decreases with increasing quantity of solvent. However, too much solvent can result in an excessive reduction in viscosity. Finally, the cold cloud point and clear point of the cleaner according to the invention decrease with increasing quantity of solvent.

The components of the cleaner according to the invention may advantageously contain one or more enzymes, above all selected from the group consisting of proteases, polysaccharidases and nucleases. The polysaccharidase may be, in particular, a β-glucanase, cellulase, xylanase, amylase, dextranase, glucosidase, galactosidase, pectinase, chitinase, lysozyme and/or alginate-lyase. The protease may be, in particular, subtilisin, thermolysin, pepsin, a carboxypeptidase and/or an acidic protease. The nucleases may be any DNAse or RNAse.

In addition, the cleaner according to the invention may optionally contain biocides.

Suitable solvents are, for example, saturated or unsaturated, preferably saturated, branched or unbranched $C_{1-20}$ hydrocarbons, preferably $C_{2-15}$ hydrocarbons, with at least one hydroxy group and optionally one or more ether functions C—O—C, i.e. oxygen atoms interrupting the carbon atom chain. However, preferred solvents are the $C_{2-6}$ alkylene glycols and poly-$C_{2-3}$-alkylene glycol ethers—optionally etherified at one end with a $C_{1-6}$ alkanol—with on average 1 to 9 identical or different, preferably identical, alkylene glycol groups per molecule, for example, ethylene glycol, propylene glycol, butylene glycol, diethylene glycol, dimethoxy glycol, dipropylene glycol, propylene glycol butyl ether, propylene glycol propyl ether, dipropylene glycol monomethyl ether and PEG. Other preferred solvents are the $C_{1-6}$ alcohols, such as methanol, ethanol, n-propanol, isopropanol, n-butanol, t-butanol, etc. Ethanol and/or isopropanol is/are particularly preferred.

Besides the solvents described above, other suitable solubilizers are, for example, alkanolamines and alkyl benzene sulfonates containing 1 to 3 carbon atoms in the alkyl group, for example, xylene or cumene sulfonate. Other suitable hydrotropes are, for example, octyl sulfate or butyl glucoside. The cleaner according to the invention may contain these hydrotropes in quantities of up to 4% by weight, based on the composition as a whole.

In one embodiment, the cleaners according to the invention may contain abrasives, The abrasive component may be selected from solid, water-soluble and water-insoluble, preferably inorganic compounds and mixtures thereof. Such compounds include, for example, alkali metal carbonates, alkali metal bicarbonates and alkali metal sulfates, alkali metal borates, alkali metal phosphates, silicon dioxide, crystalline or amorphous alkali metal silicates and layer silicates, finely crystalline sodium aluminium silicates and calcium carbonate. The advantage of water-soluble abrasive components is that the cleaner can be rinsed off with hardly any residue left behind. Besides these inorganic abrasives, naturally occurring abrasives, for example, ground-up nut shells or woods, and abrasion-resistant plastics, for example, polyethylene beads, or even ceramic or glass beads may be used. The cleaner according to the invention may contain abrasives in quantities of up to 2% by weight, based on the composition as a whole.

Besides the components mentioned, the cleaners according to the invention may contain one or more other auxiliaries and additives of the type typically encountered, above all, in hard surface cleaners. Such auxiliaries and additives include, in particular, UV stabilizers, corrosion inhibitors, cleaning boosters, antistatic agents, preservatives (for example, 2-bromo-2-nitropropane-1,3-diol or an isothiazolinone/bromonitropropane diol preparation), perfume, dyes, pearlizers (for example, glycol distearate) and opacifiers or even skin-care agents as described, for example, in EP 522 506. The quantity of such additives in the cleaner is not normally above 12% by weight. The lower limit to the quantity used depends upon the nature of the additive and, in the case of dyes for example, can be as low as 0.001% by weight or lower. The quantity of auxiliaries is preferably between 0.01 and 7% by weight and more particularly between 0.1 and 4% by weight.

Suitable dyes are any of the dyes typically used in household cleaners. The perfume may also be selected from any of the usual types. Fruity notes, for example, citrus, pine and mint, and flowery notes are preferred.

The cleaner according to the invention does not have to contain complexing or bleaching agents, such as sodium hypochlorite for example, although they may optionally be present in low concentrations.

The cleaner may contain one or more propellants (INCI Propellants), typically in a quantity of 1 to 80% by weight, more particularly in a quantity of 1.5 to 30% by weight, preferably in a quantity of 2 to 10% by weight, more preferably in a quantity of 2.5 to 8% by weight and most preferably in a quantity of 3 to 6% by weight.

According to the invention, propellants are typically propellent gases, more particularly liquefied or compressed gases. The choice is governed by the product to be sprayed and the field of application. Where compressed gases, such as nitrogen, carbon dioxide or dinitrogen oxide, which are generally insoluble in the liquid cleaner, are used, the operating pressure falls each time the valve is actuated. Liquefied gases (liquid gases) soluble in the cleaner or acting as solvents themselves afford the advantage as propellants of a constant operating pressure and a uniform distribution because the propellant evaporates in the air and, in the process, occupies several hundred times the volume.

Accordingly, the following propellants (INCI names) are suitable: Butane, Carbon Dioxide, Dimethyl Carbonate, Dimethyl Ether, Ethane, Hydrochlorofluorocarbon 22, Hydrochlorofluorocarbon 142b, Hydrofluorocarbon 152a, Hydrofluorocarbon 134a, Hydrofluorocarbon 227ea, Isobutane, Isopentane, Nitrogen, Nitrous Oxide, Pentane, Propane.

In a preferred embodiment, however, chlorofluorocarbons (fluorochlorohydrocarbons, FCHCs) as propellants are used to only a minimal extent, if at all, on account of their harmful effect on the ozone shield of the atmosphere, the so-called ozone layer, which protects us against hard UV radiation.

Preferred propellants are liquid gases. Liquid gases are gases which can be converted from the gaseous to the liquid state at generally low pressures/20° C. More particularly, however, liquid gases are understood to be the hydrocarbons propane, propene, butane, butene, isobutane (2-methylpropane), isobutene (2-methylpropane, isobutylene) and mixtures thereof which accumulate in oil refining as by-products of the distillation and cracking of petroleum and during the separation of benzene in the production of natural gas.

In a particularly preferred embodiment, the cleaner contains propane, butane and/or isobutane, more particularly propane and butane and most preferably propane, butane and isobutane as one or more propellants.

The present invention also relates to a process for cleaning hard surfaces in the home, optionally using a product according to the invention (multicompartment system), in which the low-viscosity solutions are applied to the surface to be cleaned and are then rinsed off with clean water, optionally after a reasonable contact time. The high-viscosity liquid may also be wiped or rubbed onto the surface with a cloth, sponge, brush or other utensil suitable for cleaning before rinsing off, which improves the cleaning performance, for example, where abrasives are present in the cleaner. Finally, the surface is optionally dried off with a dry cloth. If the surface is heavily soiled, the cleaning process may then be repeated.

Hair-Care Preparations

For use as body care preparations, more particularly hair-care preparations, other constituents selected in particular, from mild surfactants, oil components, emulsifiers, superfatting agents, pearlizing waxes, consistency factors, thickeners, polymers, silicone compounds, fats, waxes, stabilizers, biogenic agents, antidandruff agents, film formers, swelling agents, antioxidants, hydrotropes, preservatives, solubilizers, perfume oils and dyes may be present.

Typical examples of suitable mild, i.e. particularly dermatologically compatible, surfactants are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, α-olefin sulfonates, ether carboxylic acids, alkyl oligoglucosides, fatty acid glucamides, alkylamidobetaines and/or protein fatty acid condensates, preferably based on wheat proteins.

Suitable oil components are, for example, Guerbet alcohols based on fatty alcohols containing 6 to 18 and preferably 8 to 10 carbon atoms, esters of linear $C_{6-22}$ fatty acids with linear $C_{6-22}$ fatty alcohols, esters of branched $C_{6-13}$ carboxylic acids with linear $C_{6-22}$ fatty alcohols such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_{6-22}$ fatty acids with branched alcohols, more particularly 2-ethyl hexanol, esters of hydroxycarboxylic acids with linear or branched $C_{6-22}$ fatty alcohols, more especially Dioctyl Malate, esters of linear and/or branched fatty acids with polyhydric alcohols (for example, propylene glycol, dimer diol or trimer triol) and/or Guerbet alcohols, triglycerides based on $C_{6-10}$ fatty acids, liquid mono-, di- and triglyceride mixtures based on $C_{6-18}$ fatty acids, esters of $C_{6-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, linear and branched $C_{6-22}$ fatty alcohol carbonates, Guerbet carbonates, esters of benzoic acid with linear and/or branched $C_{6-22}$ alcohols (for example, Finsolv® TN), linear or branched, symmetrical or nonsymmetrical dialkyl ethers containing 6 to 22 carbon atoms per alkyl group, ring opening products of epoxidized fatty acid esters with polyols, silicone oils and/or aliphatic or naphthenic hydrocarbons, for example, squalane, squalene or dialkyl cyclohexanes.

Suitable emulsifiers are, for example, nonionic surfactants from at least one of the following groups:

(1) Products of the addition of 2 to 30 mol ethylene oxide and/or 0 to 5 mol propylene oxide onto linear fatty alcohols containing 8 to 22 carbon atoms, onto fatty acids containing 12 to 22 carbon atoms, onto alkylphenols containing 8 to 15 carbon atoms in the alkyl group and alkyl amines containing 8 to 22 carbon atoms in the alkyl group;

(2) $C_{12/18}$ fatty acid monoesters and diesters of products of the addition of 1 to 30 mol ethylene oxide onto glycerol;

(3) Glycerol monoesters and diesters and sorbitan monoesters and diesters of saturated and unsaturated fatty acids containing 6 to 22 carbon atoms and ethylene oxide adducts thereof;

(4) Alkyl and/or alkenyl mono- and oligoglycosides containing 8 to 22 carbon atoms in the alkyl group and ethoxylated analogs thereof;

(5) Products of the addition of 15 to 60 mol ethylene oxide onto castor oil and/or hydrogenated castor oil;

(6) Polyol esters and, in particular, polyglycerol esters;

(7) Products of the addition of 2 to 15 mol ethylene oxide onto castor oil and/or hydrogenated castor oil;

(8) Partial esters based on linear, branched, unsaturated or saturated $C_{6/22}$ fatty acids, ricinoleic acid and 12-hydroxystearic acid and glycerol, polyglycerol, pentaerythritol, dipentaerythritol, sugar alcohols (for example, sorbitol), alkyl glucosides (for example, methyl glucoside, butyl glucoside, lauryl glucoside) and polyglucosides (for example, cellulose);

(9) Mono-, di- and trialkyl phosphates and mono-, di- and/or tri-PEG-alkyl phosphates and salts thereof;

(10) Wool wax alcohols;

(11) Polysiloxane/polyalkyl polyether copolymers and corresponding derivatives;

(12) Mixed esters of pentaerythritol, fatty acids, citric acid and fatty alcohol according to DE 1165574 PS and/or mixed esters of fatty acids containing 6 to 22 carbon atoms, methyl glucose and polyols, preferably glycerol or polyglycerol,

(13) Polyalkylene glycols and

(14) Glycerol carbonate.

The addition products of ethylene oxide and/or propylene oxide onto fatty alcohols, fatty acids, alkylphenols, glycerol monoesters and diesters and sorbitan monoesters and diesters of fatty acids or onto castor oil are known, commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as lipid layer enhancers for cosmetic preparations from DE-PS 20 24 051.

Alkyl and/or alkenyl mono- and oligoglycosides, their production and their use are known from the prior art. They are produced in particular, by reacting glucose or oligosaccharides with primary alcohols containing 8 to 18 carbon atoms. So far as the glycoside unit is concerned, both monoglycosides in which a cyclic sugar unit is attached to the fatty alcohol by a glycoside bond and oligomeric glycosides with a degree of oligomerization of preferably up to about 8 are suitable. The degree of oligomerization is a statistical mean value on which the homolog distribution typical of such technical products is based.

Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera Bellina®)), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof.

Other suitable emulsifiers are zwitterionic surfactants. Zwitterionic surfactants are surface-active compounds which contain at least one quaternary ammonium group and at least one carboxylate and one sulfonate group in the molecule. Particularly suitable zwilterionic surfactants are the so-called betaines, such as the N-alkyl-N,N-dimethyl ammonium glycinates, for example, cocoalkyl dimethyl ammonium glycinate, N-acylaminopropyl-N,N-dimethyl ammonium glycinates, for example, cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine. Besides ampholytic emulsifiers, quaternary emulsifiers are also suitable, those of the esterquat type, preferably methyl-quaternized difatty acid triethanolamine ester salts, being particularly preferred.

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

Suitable pearlizing waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxysubstituted carboxylic acids with fatty alcohols containing 6 to 22 carbon atoms, especially long-chain esters of tartaric acid; fatty compounds, such as for example, fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used.

Suitable thickeners which may optionally be present in small quantities are, for example, Aerosil types (hydrophilic silicas), polysaccharides, more especially xanthan gum, guar guar, agar agar, alginates and tyloses, carboxymethyl cellulose and hydroxyethyl cellulose, also relatively high molecular weight polyethylene glycol monoesters and diesters of fatty acids, polyacrylates (for example, Carbopols® from Goodrich or Synthalens® from Sigma), polyacrylamides, polyvinyl alcohol and polyvinyl pyrrolidone, surfactants such as, for example, ethoxylated fatty acid glycerides, esters of fatty acids with polyols, for example, pentaerythritol or trimethylol propane, narrow-range fatty alcohol ethoxylates or alkyl oligoglucosides and electrolytes, such as sodium chloride and ammonium chloride.

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryidimonium Hydroxypropyl Hydrolyzed Collagen (Lamequat® L, Grünau), quaternized wheat polypeptides, polyethyleneimine, cationic silicone polymers such as, for example, amodimethicone, copolymers of adipic acid and dimethylaminohydroxypropyl diethylenetriamine (Cartaretine®, Sandoz), copolymers of acrylic acid with dimethyl diallyl ammonium chloride (Merquat® 550, Chemviron), polyaminopolyamides as described, for example, in FR 2 252 840 A and crosslinked water-soluble polymers thereof, cationic chitin derivatives such as, for example, quaternized chitosan, optionally in microcrystalline distribution, condensation products of dihaloalkyls, for example, dibromobutane, with bis-dialkylamines, for example, bis-dimethylamino-1,3-propane, cationic guar gum such as, for example, Jaguar®CBS, Jaguar®C-17, Jaguar®C-16 of Celanese, quaternized ammonium salt polymers such as, for example, Mirapol®A-15, Mirapol® AD-1, Mirapol® AZ-1 of Miranol.

Suitable anionic, zwilterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in Cosm. Toil. 91, 27 (1976).

Typical examples of fats are glycerides. Suitable waxes are, interalia, natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes.

Metal salts of fatty acids such as, for example, magnesium, aluminium and/or zinc stearate or ricinoleate may be used as stabilizers.

In the context of the invention, biogenic agents are, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

Basically, suitable germ inhibitors—which may optionally be added to the cosmetic preparations according to the invention in addition to the patchouli oil, patchouli alcohol and/or derivatives thereof used to inhibit the adhesion of microorganisms—are any substances which act against gram-positive bacteria such as, for example, 4-hydroxybenzoic acid and salts and esters thereof, N-(4-chlorophenyl)-N'-(3,4-dichlorophenyl)-urea, 2,4,4'-trichloro-2'-hydroxydiphenylether (triclosan), 4-chloro-3,5-dimethylphenol, 2,2'-methylenebis-(6-bromo-4-chlorophenol), 3-methyl-4-(1-methylethyl)-phenol, 2-benzyl-4-chlorophenol, 3-(4-chlorophenoxy)-propane-1,2-diol, 3-iodo-2-propinyl butyl carbamate, chlorhexidine, 3,4,4'-trichlorocarbanilide (TTC), antibacterial perfumes, menthol, mint oil, phenoxyethanol, glycerol monolaurate (GML), diglycerol monocaprate (DMC), salicylic acid-N-alkylamides such as, for example, salicylic acid-n-octyl amide or salicylic acid-n-decyl amide.

Enzyme inhibitors may also be added to the cosmetic preparations according to the invention. For example, esterase inhibitors are possibly suitable enzyme inhibitors. Esterase inhibitors are preferably trialkyl citrates, such as trimethyl citrate, tripropyl citrate, triisopropyl citrate, tributyl citrate and, in particular, triethyl citrate (Hydagen® CAT, Henkel KGaA, Düsseldorf, FRG). Esterase inhibitors inhibit enzyme activity and thus reduce odor formation. Other esterase inhibitors are sterol sulfates or phosphates such as, for example, lanosterol, cholesterol, campesterol, stigmasterol and sitosterol sulfate or phosphate, dicarboxylic acids and esters thereof, for example, glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example, citric acid, malic acid, tartaric acid or tartaric acid diethyl ester, and zinc glycinate.

Climbazole, octopirox and zinc pyrithione may be used as antidandruff agents. The preparations according to the invention may preferably be used in combination with at least one of these antidandruff agents for controlling dandruff.

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Suitable swelling agents for aqueous phases are montmorillonites, clay minerals, Pemulen and alkyl-modified Carbopol types (Goodrich). Other suitable polymers and swelling agents can be found in R. Lochhead's review in Cosm. Toil. 108, 95 (1993).

In addition, hydrotropes, for example, ethanol, isopropyl alcohol or polyols, may be used to improve flow behavior. Suitable polyols preferably contain 2 to 15 carbon atoms and at least two hydroxyl groups. The polyols may contain other functional groups, more especially amino groups, or may be modified with nitrogen. Typical examples are glycerol;
alkylene glycols such as, for example, ethylene glycol, diethylene glycol, propylene glycol, butylene glycol, hexylene glycol and polyethylene glycols with an average molecular weight of 100 to 1,000 dalton;
technical oligoglycerol mixtures with a degree of self-condensation of 1.5 to 10 such as, for example, technical diglycerol mixtures with a diglycerol content of 40 to 50% by weight;
methylol compounds such as, in particular, trimethylol ethane, trimethylol propane, trimethylol butane, pentaerythritol and dipentaerythritol;
lower alkyl glucosides, particularly those containing 1 to 8 carbon atoms in the alkyl group, for example, methyl and butyl glucoside;
sugar alcohols containing 5 to 12 carbon atoms, for example, sorbitol or mannitol,
sugars containing 5 to 12 carbon atoms, for example, glucose or sucrose;
amino sugars, for example, glucamine;
dialcoholamines, such as diethanolamine or 2-aminopropane-1,3-diol.

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive"). Suitable insect repellents are N,N-diethyl-m-toluamide, pentane-1,2-diol or Ethyl Butylacetylaminopropionate. A suitable self-tanning agent is dihydroxyacetone.

Suitable perfume oils are mixtures of natural and synthetic perfumes. Natural perfumes include the extracts of blossoms (lily, lavender, rose, jasmine, neroli, ylang-ylang), stems and leaves (geranium, petitgrain), fruits (anise, coriander, caraway, juniper), fruit peel (bergamot, lemon, orange), roots (nutmeg, angelica, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example, civet and beaver, may also be used. Typical synthetic perfume compounds are products of the ester, ether, aldehyde, ketone, alcohol and hydrocarbon type.

Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemie, Weinheim, 1984, pages 81 to 106. These dyes are normally used in concentrations of 0.001 to 0.1% by weight, based on the mixture as a whole.

The total percentage content of auxiliaries and additives may be from 1 to 50% by weight and is preferably from 5 to 40% by weight, based on the particular formulation. The preparations may be produced by standard hot or cold processes and are preferably produced by the phase inversion temperature method.

Laundry Pretreatment Preparations

For use as a laundry pretreatment preparation, other components known to the expert besides the hydrophobically modified polymer and the above-mentioned surfactants may be present in the laundry pretreatment preparation. These other components may be, for example, hydrophobic components, builders, enzymes, perfume/fragrances, dyes or emulsion aids or combinations thereof.

Suitable hydrophobic components are any known oils, fats and waxes of mineral, animal, vegetable and synthetic origin. Oil and fatty components, above all liquid hydrocarbons containing 10 to 32 carbon atoms, fatty acid esters containing a total of 12 to 26 carbon atoms and mixtures thereof are preferred. Suitable hydrocarbons are, above all, paraffins and isoparaffins, such as isohexadecane or n-dodecane, and others, for example, triisobutene, pentapropylene or 1,3-di-(2-ethylhexyl)-cyclohexane. Suitable fatty acid esters are, for example, such substances as methyl oleate, methyl palmitate, ethyl oleate, isopropyl myristate, n-hexyl laurate, n-butyl stearate, glycerol monooleate, glycerol monostearate and cetyl/stearyl isononaoate. In a preferred embodiment, isoparaffin mixtures are used as the hydrophobic component. Suitable isoparaffin mixtures are, for example, the $C_{16-20}$ isoparaffins marketed under the names of Cobersol® VPI or Cobersol® B 105 (CBR) or the $C_{12-14}$ isoparaffin mixture Isopar® M (Exxon Mobil). Other substances which may be used as hydrophobic components are dialkyl ethers containing a total of 12 to 24 carbon atoms. Preferred dialkyl ethers are, above all, the aliphatic dialkyl ethers containing 6 to 10 carbon atoms per alkyl group. In addition, any other known oil components, such as Vaseline, vegetable oils, synthetic triglycerides, such as glyceryl tricaprylate for example, and also fats and waxes and silicone oils may be present in the microemulsions according to the invention. In a preferred embodiment of the invention, hydrophobic components, preferably paraffins, are used in quantities of 5 to 70% by weight and more particularly in quantities of 8 to 52% by weight, based on the microemulsion as a whole.

If, in addition to paraffin oils, glycerol monoesters are used in quantities of 0 to 15% by weight and preferably in quantities of 1 to 10% by weight, based on the microemulsion as a whole, thickening of the microemulsion according to the invention can occur which is an advantage in the intended use of the microemulsion by virtue of the higher viscosities thus established. Microemulsions thus thickened can have viscosities of 1,000 to 10,000 mPas at a shear rate of 30 $s^{-1}$ and a temperature of 20° C. Any other thickeners typically used in detergents and cleaners, for example, organic natural thickeners (agar agar, carrageen, tragacanth, gum arabic, alginates, pectins, polyoses, guar flour, locust bean gum, starch, dextrins, gelatin, casein), organic modified natural substances (carboxymethyl cellulose and other cellulose ethers, hydroxyethyl and hydroxypropyl cellulose and the like, gum ethers), organic fully synthetic thickeners (polyacrylic and polymethacrylic compounds, vinyl polymers, polycarboxylic acids, polyethers, polyimines, polyamides) and inorganic thickeners (polysilicic acids, clay minerals, such as montmorillonites, zeolites, silicas) may also be used for the microemulsion according to the invention. However, preferred thickeners are glycerol monoesters of fatty acids, more particularly the glycerol monooleate marketed, for example, under the name of Monomuls® 90-O18 by Cognis, glycerol monostearate, for example, Cutina® GMS marketed by Cognis, and mixtures thereof.

Suitable builders are, for example, citric acid, alkali metal citrates, gluconates, nitrilotriacetates, carbonates and bicarbonates, more particularly sodium citrate, gluconate and nitrilotriacetate and sodium and potassium carbonate and bicarbonate and mixtures thereof. Other suitable builders are the salts of glutaric acid, succinic acid, adipic acid, tartaric acid and benzene hexacarboxylic acid and also phosphonates and phosphates, for example, sodium hexametaphosphate. The pre-spotting preparations may contain builders in quantities of 0 to 30% by weight, based on the composition.

Suitable bleaching agents are any of the bleaching agents typically used in detergents and cleaners. However, hydrogen peroxide or phthalimidoperoxycaproic acid is preferably used as the bleaching agent. The laundry pretreatment preparation may contain bleaching agents in quantities of 0 to 30% by weight.

In one particular embodiment of the invention, the microemulsion contains one or more optionally stabilized enzymes.

The pre-spotting preparation according to the invention may contain one or more different amylolytic enzymes, more particularly α-amylases. Examples of commercially available amylases are BAN®, Termamyl®, Purastar®, Amylase-LT®, Maxamyl®, Duramyl® and/or Purafect® Ox-Am.

It can be of advantage to use several different washing- and/or cleaning-active enzymes, particularly against chemically diverse soils. These include, for example, proteases and also lipases, cutinases, esterases, pullulanases, cellulases, hemicellulases and/or xylanases and mixtures thereof. Proteases, lipases, β-glucanases and/or cellulases are particularly preferred. Other enzymes extend the cleaning performance of corresponding preparations by their specific enzymatic activity. These include, for example, oxidoreductases or peroxidases as components of enzymatic bleaching systems, for example, laccases (WO 00/39306), β-glucanes (WO 99/06515 and WO 99/06516) or pectin-dissolving enzymes (WO 00/42145) which are used in particular, in special-purpose preparations.

Examples of commercially obtainable enzymes for use in the laundry pretreatment preparations according to the invention are proteases, such as subtilisin BPN', Properase®, alkaline protease from Bacillus lentus, Optimase®, Opticlean®, Maxatase®, Maxacal®, Maxapem®, Alcalase®, Esperase®, Savinase®, Durazym®, Everlase® and/or Purafect®G or Purafect®OxP, and lipases, such as Lipolase®, Lipomax®, Lumafast® and/or Lipozym®. The protease activity in such preparations can be determined by the method described in Tenside, Vol. 7 (1970), pp. 125-132. Accordingly, it is expressed in PU (protease units). The protease activity of preferred preparations can be up to 1,500,000 protease units per gram of preparation (PU, as determined by the method described in Tenside, Vol. 7 (1970), pp. 125-132).

These optionally additionally used enzymes may be adsorbed onto carriers and/or encapsulated in membrane materials to protect them against premature deactivation, as described, for example, in European patent EP 0 564 476 or in International Patent Application WO 94/23005. They are present in laundry detergents in quantities of preferably up to 10% by weight and more particularly in quantities of 0.2% by weight to 2% by weight. A particularly preferred embodiment is characterized by the use of enzymes stabilized against oxidative degradation, as known for example, from International Patent Application WO 94/18314.

The pre-spotting preparations may contain enzymes in quantities of 0 to 3% by weight.

Emulsion aids which may be used in the preparations according to the invention emanate, for example, from the group of mono- or polyhydric alcohols, alkanolamines or glycol ethers, providing they are miscible with water in the concentration range indicated. The solvents are preferably selected from water-soluble mono- or polyhydric alcohols containing 1 to 8 carbon atoms, for example, methanol, ethanol, n- or i-propanol, butanols, n-hexanol, n-octanol, glycol, propane or butane diol, glycerol, diglycol, propyl or butyl diglycol, hexylene glycol, ethylene glycol methyl ether, ethylene glycol ethyl ether, ethylene glycol propyl ether, ethylene glycol mono-n-butyl ether, diethylene glycol methyl ether, diethylene glycol ethyl ether, propylene glycol methyl, ethyl or propyl ether, butoxypropoxy butanol (BPP), dipropylene glycol monomethyl or monoethyl ether, diisopropylene glycol monomethyl or monoethyl ether, methoxy, ethoxy or butoxy triglycol, 1-butoxyethoxy-2-propanol, 3-methyl-3-methoxybutanol, propylene glycol-t-butyl ether and mixtures of these solvents. Monohydric alcohols are preferably used, more particularly ethanol in quantities of 0 to 30% by weight and preferably 0 to 14.5% by weight and/or n-hexanol/n-octanol in quantities of 0 to 10% and preferably 0 to 5%.

Other organic solvents suitable in principle are standard halogenated solvents as typically known from institutional dry cleaning. These solvents include, inter alia, the di- to tetrachlorinated derivatives of methane, the di- to pentachlorinated derivatives of ethane, the mono- to trichlorinated derivatives of cyclohexane and monochlorobenzene. Special examples are carbon tetrachloride, methylene chloride, 1,1-dichloroethane, 1,2-dichloroethane, 1,1,1-trichloroethane, 1,1,2-trichloroethane, trichloroethene, 1,1,2,2-tetrachloroethane, tetrachloroethene, pentachloroethane, monochlorocyclohexane, 1,4-dichlorocyclohexane, monochlorobenzene and mixtures of the above. However, these chlorinated hydrocarbons are not preferred for use in the home.

The pre-spotting preparation may additionally contain dyes. Any dyes typically used in laundry detergents and cleaners are suitable. The dyes may be used in particular, in quantities of 0 to 0.5% by weight.

The preparation according to the invention may additionally contain perfume or fragrances. Any of the substances typically used as such in laundry detergents and cleaners may be used, preferably perfume oils in quantities of 0 to 70% by weight and more particularly in quantities of 0 to 16% by weight.

In a second embodiment, the present invention relates to the use of the fabric pretreatment preparation for pretreating fabrics.

The pre-spotting preparation is particularly suitable for the targeted pretreatment of stains on various fabrics. Thus, articles of clothing and textile articles of nonwovens, felts, woven or knitted fabrics of natural and manmade fibers, such as cotton, wool, silk, linen, artificial silks, for example, viscose, polyamide, polyacrylic, polyester, polyvinyl chloride, elasthane and any other typically used fibers and blends thereof may be contacted with the pre-spotting preparation according to the invention over the soiled areas.

The present invention also relates to a process for removing stains on textiles using a pre-spotting preparation according to the invention.

The pre-spotting preparation is used by applying it to the stain, preferably using one of the above-mentioned applicators, and leaving it for preferably 5 to 15 minutes. In a particularly preferred embodiment, the pre-spotting preparation is rubbed onto the stain. It is then either rinsed out with clean water or the textile article is subsequently washed.

EXAMPLES

The viscosity values shown were taken from the flow tests where:
$\eta_{0.1s}-1$ = viscosity at a shear rate of $0.1\ s^{-1}$ in Pas
$\eta_{1s}-1$ = viscosity at a shear rate of $1\ s^{-1}$ in Pas
$\eta_{100s}-1$ = viscosity at a shear rate of $100\ s^{-1}$ in Pas.

The % by weight values mentioned in the following for the surfactants Texapon K12, Texapon NSO and Dehydol LS6 relate to the surfactant content used and not to the weight of the products used as a whole. Texapon K12 contains 96% by weight, Texapon NSO 27% by weight and Dehydol LS6 98.2% by weight of surfactant.

Example 1

Component 1:
2% by weight hydrophobically modified polyacrylate (molecular weight of the polyacrylic acid: 150 kDa, degree of modification: 3% with $C_{18}$)
Rest deionized water
pH 9-10

Component 2:
2% by weight hydrophobically modified polyacrylate (as in component 1)
2% by weight SDS (Texapon K12 96%, Cognis, Germany)
Rest deionized water
pH 9-10

Components 1 and 2 were mixed in a ratio of 9:1. The resulting pH value was 9-10.

| Sample | Composition | $\eta_{0.1s}-1$ (Pas) | $\eta_{1s}-1$ (Pas) | $\eta_{100s}-1$ (Pas) |
|---|---|---|---|---|
| Component 1 | 2% PA 150 kDa | 0.03 | 0.03 | 0.02 |
| Component 2 | 2% PA 150 kDa + 2% SDS | 0.05 | 0.05 | 0.04 |
| Mixture 9:1 | 2% PA 150 kDa + 0.2% SDS | 199.00 | 82.98 | 0.68 |

Example 2

Component 1:
0.5% by weight hydrophobically modified polyacrylate (molecular weight of the polyacrylic acid: 450 kDa, degree of modification 3% with $C_{18}$)
Rest deionized water
pH ~9

Component 2:
0.5% by weight hydrophobically modified polyacrylate (as in component 1)

1% by weight SDS (Texapon K12 96%, Cognis, Germany)
Rest deionized water
pH ~9

Components 1 and 2 were mixed in a ratio of 4:1. The resulting pH value was ~9.

| Sample | Composition | $\eta_{0.1\,s}-1$ (Pas) | $\eta_{1\,s}-1$ (Pas) | $\eta_{100\,s}-1$ (Pas) |
| --- | --- | --- | --- | --- |
| Component 1 | 0.5% PA 450 kDa | 0.31 | 0.23 | 0.08 |
| Component 2 | 0.5% PA 450 kDa + 1% SDS | 25.29 | 4.48 | 0.25 |
| Mixture 4:1 | 0.5% PA 450 kDa + 0.2% SDS | 254.50 | 37.61 | 0.79 |

Example 3

Component 1:
2% by weight Acusol 801 S (Rohm and Haas) (corresponds to 0.4% by weight hydrophobically modified polymer)
Rest deionized water
pH ~9-10

Component 2:
2% by weight Acusol 801 S (Rohm and Haas) (corresponds to 0.4% by weight hydrophobically modified polymer)
1% by weight SDS (Texapon K12 96%, Cognis, Germany)
Rest deionized water
pH ~8

Components 1 and 2 were mixed in a ratio of 4:1. The resulting pH value was ~8.

| Sample | Composition | $\eta_{0.1\,s}-1$ (Pas) | $\eta_{1\,s}-1$ (Pas) | $\eta_{100\,s}-1$ (Pas) |
| --- | --- | --- | --- | --- |
| Component 1 | 2% Acusol 801 S | 33.78 | 4.27 | 0.13 |
| Component 2 | 2% Acusol 801 S + 1% SDS | 1.90 | 0.82 | 0.05 |
| Mixture 4:1 | 2% Acusol 801 S + 0.2% SDS | 411.60 | 30.99 | 0.64 |

Example 4

Component 1:
3.3% by weight Acusol 820 (Rohm and Haas, Germany) (corresponds to 1% by weight hydrophobically modified polymer)
Rest deionized water
pH ~6-8

Component 2:
3.3% by weight Acusol 820 (Rohm and Haas, Germany) (corresponds to 1% by weight hydrophobically modified polymer)
10% by weight SDS (sodium dodecyl sulfate; Texapon K12 96%, Cognis, Germany) Rest deionized water
pH ~10

Components 1 and 2 were mixed in a ratio of 49:1. The resulting pH value was 6-7.

| Sample | Composition | $\eta_{0.1\,s}-1$ (Pas) | $\eta_{1\,s}-1$ (Pas) | $\eta_{100\,s}-1$ (Pas) |
| --- | --- | --- | --- | --- |
| Component 1 | 3.3% Acusol 820 | 185.70 | 29.27 | 0.83 |
| Component 2 | 3.3% Acusol 820 + 10% SDS | 1.46 | 1.29 | 0.18 |
| Mixture 49:1 | 3.3% Acusol 820 + 0.2% SDS | 332.20 | 72.92 | 5.13 |

Example 5

Component 1:
3.3% by weight Acusol 820 (Rohm and Haas, Germany) (corresponds to 1% by weight hydrophobically modified polymer)
Rest deionized water
pH ~6-7

Component 2:
3.3% by weight Acusol 820 (Rohm and Haas, Germany) (corresponds to 1% by weight hydrophobically modified polymer)
2% by weight SDS (sodium dodecyl sulfate; Texapon K12 96%, Cognis, Germany)
Rest deionized water
pH ~7

Components 1 and 2 were mixed in a ratio of 9:1. The resulting pH value was ~7.

| Sample | Composition | $\eta_{0.1\,s}-1$ (Pas) | $\eta_{1\,s}-1$ (Pas) | $\eta_{100\,s}-1$ (Pas) |
|---|---|---|---|---|
| Component 1 | 3.3% Acusol 820 | 194.30 | 31.70 | 0.72 |
| Component 2 | 3.3% Acusol 820 + 2% SDS | 76.79 | 36.68 | 0.87 |
| Mixture 9:1 | 3.3% Acusol 820 + 0.2% SDS | 392.20 | 150.40 | 2.96 |

Example 6

Component 1:
2% by weight Acusol 801 S (Rohm and Haas, Germany)
  (corresponds to 0.4% by weight hydrophobically modified polymer)
Rest deionized water
pH ~11

Component 2:
2% by weight Acusol 801 S (Rohm and Haas, Germany)
  (corresponds to 0.4% by weight hydrophobically modified polymer)
0.5% by weight Texapon NSO (Cognis, Germany)
Rest deionized water
pH ~8

Components 1 and 2 were mixed in a ratio of 4:1. The resulting pH value was ~9.

| Sample | Composition | $\eta_{0.1\,s}-1$ (Pas) | $\eta_{1\,s}-1$ (Pas) | $\eta_{100\,s}-1$ (Pas) |
|---|---|---|---|---|
| Component 1 | 2% Acusol 801 S | 96.07 | 7.37 | 0.16 |
| Component 2 | 2% Acusol 801 S + 0.5% Texapon NSO | 25.32 | 6.94 | 0.11 |
| Mixture 4:1 | 2% Acusol 801 S + 0.1% Texapon NSO | 357.30 | 51.26 | 1.12 |

Example 7

Component 1:
2% by weight Acusol 801 S (Rohm and Haas, Germany)
  (corresponds to 0.4% by weight hydrophobically modified polymer)
Rest deionized water
pH ~11

Component 2:
2% by weight Acusol 801 S (Rohm and Haas, Germany)
  (corresponds to 0.4% by weight hydrophobically modified polymer)
1.5% by weight Dehydol LS6 (Cognis, Germany)
Rest deionized water
pH ~10

Components 1 and 2 were mixed in a ratio of 14:1. The resulting pH value was ~10.

| Sample | Composition | $\eta_{0.1\,s}-1$ (Pas) | $\eta_{1\,s}-1$ (Pas) | $\eta_{100\,s}-1$ (Pas) |
|---|---|---|---|---|
| Component 1 | 2% Acusol 801 S | 56.48 | 5.66 | 0.14 |
| Component 2 | 2% Acusol 801 S + 1.5% Dehydol LS6 | 16.01 | 10.24 | 1.62 |
| Mixture 14:1 | 2% Acusol 801 S + 0.1% Dehydol LS6 | 289.70 | 44.41 | 0.84 |

Example 8

Component 1:
2% by weight Acusol 801 S (Rohm and Haas, Germany)
  (corresponds to 0.4% by weight hydrophobically modified polymer)
Rest deionized water
pH ~11

Component 2:
2% by weight Acusol 801 S (Rohm and Haas, Germany)
  (corresponds to 0.4% by weight hydrophobically modified polymer)
5% by weight Dehydol LS6 (Cognis, Germany)
Rest deionized water
pH ~10

Components 1 and 2 were mixed in a ratio of 49:1. The resulting pH value was ~10.

| Sample | Composition | $\eta_{0.1\,s}-1$ (Pas) | $\eta_{1\,s}-1$ (Pas) | $\eta_{100\,s}-1$ (Pas) |
|---|---|---|---|---|
| Component 1 | 2% Acusol 801 S | 56.48 | 5.66 | 0.14 |
| Component 2 | 2% Acusol 801 S + 5% Dehydol LS6 | 6.65 | 3.73 | 1.13 |
| Mixture 49:1 | 2% Acusol 801 S + 0.1% Dehydol LS6 | 537.20 | 46.35 | 0.99 |

Example 9

Component 1:
1.0-2.5% by weight Acusol 801 S (Rohm and Haas, Germany) (corresponds to 0.4% by weight hydrophobically modified polymer)
2-10% by weight glycerol (99.5%)
2-10% by weight monoethanolamine (99%)
Sodium hydroxide (50%) for pH adjustment
Rest deionized water
pH 11-13

Component 2:
1.0-2.5% by weight Acusol 801 S (Rohm and Haas, Germany) (corresponds to 0.4% by weight hydrophobically modified polymer)
0.5-3.0% by weight Texapon LS 35 (~35%; Cognis, Germany)
0.1-1.5% by weight Dehydol LS6 (Cognis, Germany)
2-10% by weight monoethanolamine (99%)
Sodium hydroxide (50%) for pH adjustment
Rest deionized water
pH 11-13

Components 1 and 2 were mixed in a ratio of 1:1. The resulting pH value was 11-13.

The invention claimed is:

1. A multicomponent system, the system comprising:
   a) a first alkaline aqueous liquid having a pH of up to 14 and containing at least one hydrophobically modified polymer in an amount of 0.1 to 2.0% by weight; and
   b) a second alkaline aqueous liquid having a pH of up to 14 and containing at least one hydrophobically modified polymer in an amount of 0.1 to 2.0% by weight and at least one surfactant
      wherein the hydrophobically modified polymer has a molecular weight of 10 to 1,000 kDa and a degree of modification of 1 to 10%, and
      wherein the viscosity of a mixture of the first and second alkaline aqueous liquids at a shear rate of 0.1 s$^{-1}$ is at least about twice as high as the viscosity of at least one of the first or second alkaline aqueous liquids.

2. The multicomponent system as claimed in claim 1, characterized in that the hydrophobically modified polymer is selected from the group consisting of a hydrophobically modified polyacid, a hydrophobically modified polyamide and a hydrophobically modified polyalcohol.

3. The multicomponent system as claimed in claim 2, characterized in that the hydrophobically modified polyacid is a hydrophobically modified polyacrylates or polyacrylic acid amide.

4. The multicomponent system as claimed in claim 1, characterized in that the hydrophobic modification consists of alkyl groups or polyether groups.

5. The multicomponent system as claimed in claim 1, characterized in that the degree of modification of the hydrophobically modified polymer is between 2 and 5%.

6. The multicomponent system as claimed in claim 1, characterized in that the quantity of surfactant in the second liquid is between 0.05 and 20% by weight.

7. The multicomponent system as claimed in claim 1, characterized in that the at least one surfactant is selected from the group consisting of anionic surfactants, nonionic surfactants, amphoteric surfactants and zwitteronic surfactants.

8. The multicomponent system as claimed in claim 7, characterized in that the surfactant is selected from the group consisting of sulfates, alkyl ether sulfates, alkyl sulfonates, alkyl aryl sulfonates, alkyl benzene sulfonates, alkyl aryl ether sulfonates, alkyl ether oxylates, fatty alcohol ether sulfates, LAS, alkyl polyglycosides, betaines and fatty alcohol ethoxylates.

9. The multicomponent system as claimed in claim 8, characterized in that the surfactant is selected from the group consisting of dodecyl sulfate, dodecyl ether sulfate and fatty alcohol ethoxylates with an average degree of ethoxylation of less than 20 EO.

10. The multicomponent system as claimed in claim 9, characterized in that the surfactant is selected from the group consisting of dodecyl sulfate, dodecyl ether sulfate and fatty alcohol ethoxylates comprising a $C_{12-18}$ fatty alcohol and 6 to 7 ethoxylate units.

11. The multicomponent system as claimed in claim 1, characterized in that the first liquid additionally contains a surfactant.

12. The multicomponent system as claimed in claim 11, characterized in that the surfactant is present in a quantity up to 0.4% by weight.

13. The multicomponent system as claimed in claim 1, characterized in that the multicomponent system is a two-component system and the two liquids are accommodated in the two compartments of a double-compartment system.

14. The multicomponent system as claimed in claim 13, characterized in that the double-compartment system is a double-compartment bottle or a double-compartment spray.

15. A process for the production of a high-viscosity liquid comprising:
   mixing together at least two alkaline liquids having a pH of up to 14,
   wherein the first of the at least two alkaline liquids comprises 0.1 to 2.0% by weight of at least one hydrophobically modified polymer and the second of the at least two alkaline liquids comprises 0.1 to 2.0% by weight of at least one hydrophobically modified polymer and at least one surfactant, wherein the hydrophobically modified polymer has a molecular weight of 10 to 1,000 kDa and a degree of modification of 1 to 10%, wherein the viscosity of the high-viscosity liquid at a shear rate of 0.1 s$^{-1}$ is at least about twice as high as the viscosity of at least one of the first or second alkaline aqueous liquids.

16. The process as claimed in claim 15, characterized in that the hydrophobically modified polymer is selected from the group consisting of a hydrophobically modified polyacid, a hydrophobically modified polyamide and a hydrophobically modified polyalcohol.

17. The process as claimed in claim 15, characterized in that the surfactant is selected from the group consisting of an anionic surfactant, a nonionic surfactant, an amphoteric surfactant and a zwitteronic surfactant.

18. The process as claimed in claim 15, characterized in that the mixing is carried out in a multicomponent system.

19. A cosmetic preparation comprising the multicomponent system of claim 1.

20. A detergent and/or cleaning composition comprising:
a) a first alkaline aqueous liquid having a pH of up to 14 and containing at least one hydrophobically modified polymer in an amount of 0.1 to 2.0% by weight and surfactant in an amount of between 0 and 0.4% by weight; and
b) a second alkaline aqueous liquid having a pH of up to 14 and containing at least one hydrophobically modified polymer in an amount of 0.1 to 2.0% by weight and at least one surfactant wherein the hydrophobically modified polymer has a molecular weight of 10 to 1,000 kDa and a degree of modification of 1 to 10%, wherein the first and second alkaline aqueous liquids are contained in a multicomponent system, and wherein the viscosity of a mixture of the first and second alkaline aqueous liquids at a shear rate of $0.1\ s^{-1}$ is at least about twice as high as the viscosity of at least one of the first or second alkaline aqueous liquids.

\* \* \* \* \*